(12) United States Patent
Mackie

(10) Patent No.: US 12,350,119 B2
(45) Date of Patent: Jul. 8, 2025

(54) INTRA-ORAL APPLIANCE FOR DELIVERING RED, NEAR-INFRARED AND BLUE LIGHT FOR ORAL TISSUE HEALING

(71) Applicant: Kurt Mackie, Boerne, TX (US)

(72) Inventor: Kurt Mackie, Boerne, TX (US)

(*) Notice: Subject to any disclaimer, the term of this patent is extended or adjusted under 35 U.S.C. 154(b) by 804 days.

(21) Appl. No.: 17/144,254

(22) Filed: Jan. 8, 2021

(65) Prior Publication Data

US 2021/0267738 A1    Sep. 2, 2021

Related U.S. Application Data

(60) Provisional application No. 62/983,071, filed on Feb. 28, 2020.

(51) Int. Cl.
*A61C 19/06* (2006.01)
*A61N 5/06* (2006.01)

(52) U.S. Cl.
CPC ............ *A61C 19/06* (2013.01); *A61N 5/0603* (2013.01); *A61N 2005/0606* (2013.01); *A61N 2005/0651* (2013.01); *A61N 2005/0659* (2013.01); *A61N 2005/0663* (2013.01)

(58) Field of Classification Search
CPC .. A61C 19/06; A61C 19/063; A61N 5/00606; A61N 2005/0606; A61N 2005/0659; A61N 2005/0651; A61N 2005/0663; A61N 2005/0652; A61N 2005/0662
See application file for complete search history.

(56) References Cited

U.S. PATENT DOCUMENTS

| 4,852,549 | A | * | 8/1989 | Mori ....................... | B32B 27/08 |
| | | | | | 607/93 |
| 5,203,324 | A | * | 4/1993 | Kinkade ................ | B63C 11/186 |
| | | | | | 128/207.14 |
| 5,487,662 | A | * | 1/1996 | Kipke ................... | A61C 9/0006 |
| | | | | | 433/29 |
| 8,215,954 | B2 | * | 7/2012 | Levine .................. | A61C 19/066 |
| | | | | | 433/29 |
| D836,204 | S | | 12/2018 | Montgomery | |
| 2003/0004393 | A1 | * | 1/2003 | Ewing ..................... | A61N 2/06 |
| | | | | | 600/9 |
| 2004/0193236 | A1 | * | 9/2004 | Altshuler ............ | A61B 18/203 |
| | | | | | 607/88 |

(Continued)

FOREIGN PATENT DOCUMENTS

WO    2019140285 A2    7/2019

OTHER PUBLICATIONS

LED Optics Explained. LED Supply. Taylor Scully. May 2021. (Year: 2021).*

(Continued)

*Primary Examiner* — Heidi M Eide
*Assistant Examiner* — Lina Faraj
(74) *Attorney, Agent, or Firm* — Braxton Perrone, PLLC; Gregory Perrone; Bobby W. Braxton

(57) ABSTRACT

An intra-oral appliance for delivering light waves from inside the mouth directly to the oral tissues via a clear, mouthguard positioned on the user's upper and lower teeth, having a series of light emitting diodes disposed on buccal and lingual sides of the appliance and an antenna or data connector for wireless or wired control and application of light waves of a variety of wavelengths to the oral tissues via the LEDs.

12 Claims, 13 Drawing Sheets

(56) References Cited

U.S. PATENT DOCUMENTS

| | | | |
|---|---|---|---|
| 2005/0202363 A1 | 9/2005 | Osterwalder | |
| 2011/0076636 A1* | 3/2011 | Wolff | A61C 19/063 |
| | | | 433/29 |
| 2011/0104631 A1 | 5/2011 | Levine | |
| 2013/0040264 A1* | 2/2013 | Scurtescu | A61C 7/00 |
| | | | 433/119 |
| 2014/0072932 A1 | 3/2014 | Brawn et al. | |
| 2014/0272761 A1* | 9/2014 | Lowe | A61C 17/3481 |
| | | | 433/2 |
| 2014/0295377 A1 | 10/2014 | Lewis et al. | |
| 2015/0140502 A1* | 5/2015 | Brawn | A61C 7/08 |
| | | | 433/29 |
| 2017/0027675 A1 | 2/2017 | Nahshon | |
| 2017/0080249 A1 | 3/2017 | Brawn et al. | |
| 2017/0173358 A1* | 6/2017 | Demarest | A61C 19/066 |
| 2018/0178031 A1 | 6/2018 | Wu | |
| 2018/0206956 A1* | 7/2018 | Pierson | A61C 19/003 |
| 2019/0083202 A1* | 3/2019 | Brawn | A61C 8/0006 |
| 2020/0345472 A1* | 11/2020 | Chapman | A61N 5/0603 |
| 2021/0228900 A1* | 7/2021 | Kothari | A61H 21/00 |

OTHER PUBLICATIONS

Supplementary European Search Report for EP 21760476, dated Feb. 21, 2024, 3 pages.

* cited by examiner

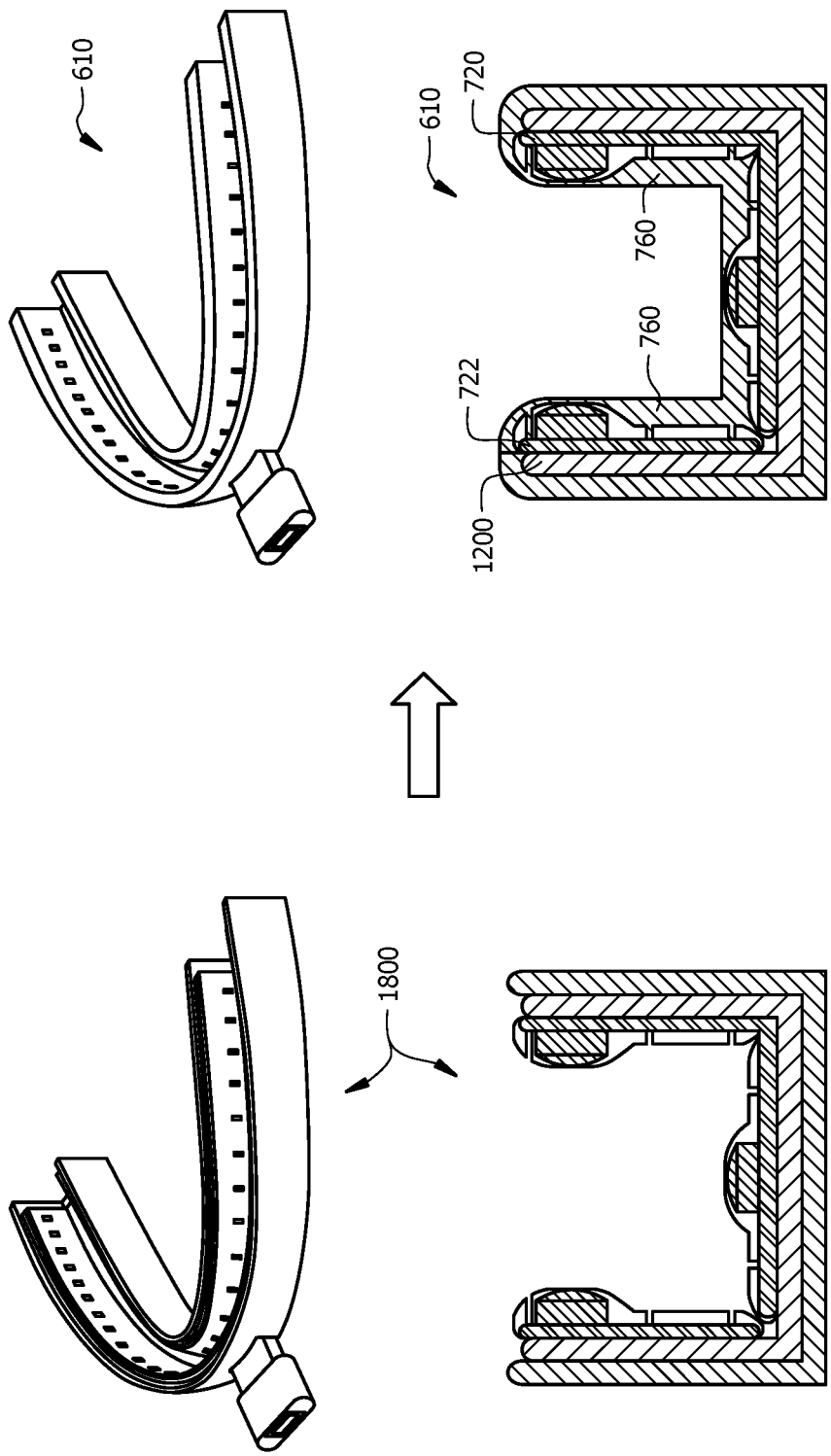

INTRA-ORAL APPLIANCE FOR DELIVERING RED, NEAR-INFRARED AND BLUE LIGHT FOR ORAL TISSUE HEALING

This Application claims priority to Provisional Application No. 62/983,071 filed Feb. 28, 2020, the entirety of which is incorporated herein by reference.

TECHNICAL FIELD

This disclosure relates generally to a system and apparatus for delivery of a range of specified wavelengths on the inside of the mouth to promote tissue healing and bone growth.

BACKGROUND

The invention presents an internal, oral device to deliver a range of specified light wavelengths on the inside the mouth to promote tissue healing and bone growth.

Currently, devices use light waves to promote oral healing, but such devices are extra-oral, i.e., they are affixed externally to the cheek or other areas of the face. The lightwaves from such devices must penetrate the cheek wall and/or other skin, bone and tooth structures of the head and oral region. As a result, the efficacy of the light waves from such devices is diminished as is their therapeutic properties. Delivering light waves from inside the mouth directly to the oral tissues as the invention proposes, is a superior delivery system vis-a-via existing extra-oral devices. Positioning the light sources closer to the target tissues improves the efficacy of this treatment protocol.

Appliances on the market today attempt to deliver light to internal mouth tissues (see U.S. Pat. No. 9,308,389 assigned to Biolux Research LTD). Such devices, however, are extra-oral devices that deliver inferior light-rays to diseased oral tissues and bone structures including the hard palate and sub-lingual tissues. It is preferable to have a completely intra-oral appliance that maintains the proper light intensity and frequency that is not lost or diffused through extra-oral and hard tissues. Existing appliances do not have the appropriate power versatility and light wavelengths to be effective within the oral cavity.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings and photographs, wherein:

FIG. 19 depicts the mouthpiece assembly resulting from a method of mouthpiece assembly of an intra-oral appliance system according to an embodiment of the present invention.

DETAILED DESCRIPTION OF THE EMBODIMENTS

The detailed description set forth below is intended as a description of the presently embodiments of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Several embodiments of Applicant's invention will now be described with reference to the drawings. Unless otherwise noted, like elements will be identified by identical numbers throughout all figures. The invention illustratively disclosed herein suitably may be practiced in the absence of any element which is not specifically disclosed herein.

Figure 1:
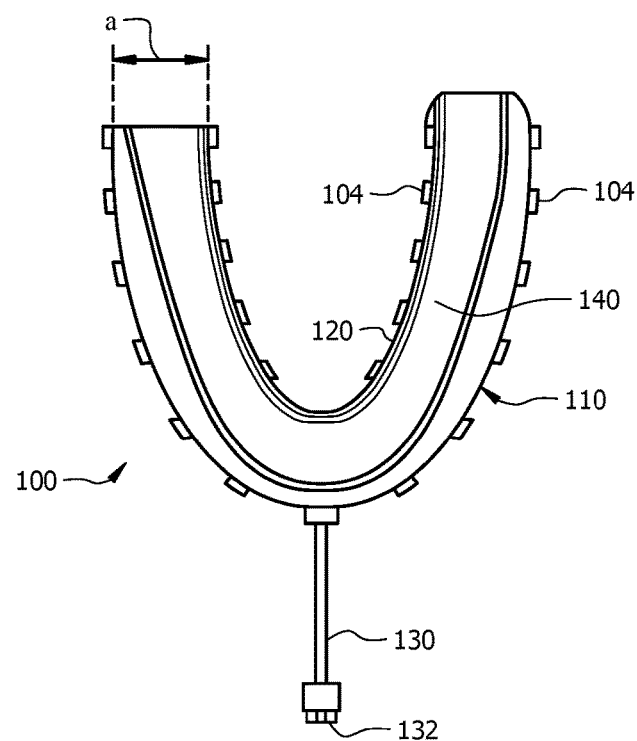
FIG. 1 depicts a top view of an intra-oral appliance according to an embodiment of the present invention.
Figure 2:
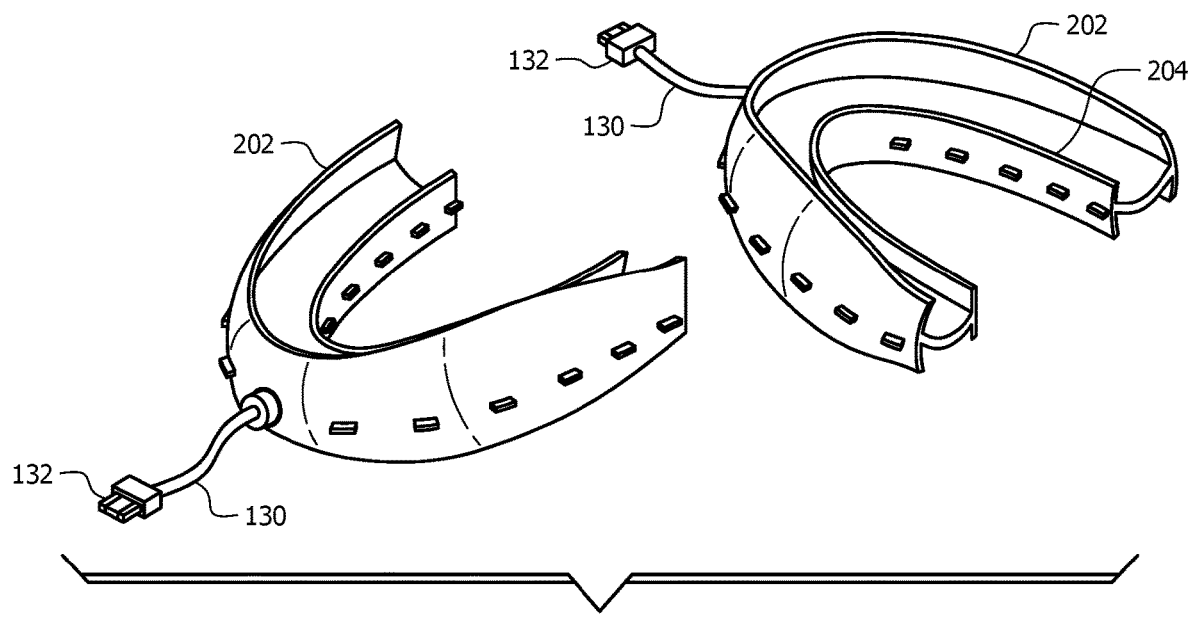
FIG. 2 depicts perspective views of an upper half and a lower half of an intra-oral appliance according to an embodiment of the present invention.

FIG. 1 depicts an embodiment of the presently described intra-oral appliance. Oral appliance 100 in one embodiment is manufactured from clear non-latex rubber formed into an arch-bite block that encircles the gums and adjacent areas of the mouth. The material is highly translucent. The light-ray treatments are delivered to the gums, interior cheeks, and related structures thought the material. Oral appliance 100 comprises a disposable barrier sleeve of clear plastic to allow proper infection control and reusability of the device. The attached drawings delineate the form and dimensions of the appliance. The lights embedded within the appliance are specialized LED lights 104 that emit specific broad range red, near-infrared and blue spectrum light. LEDs 104 will be aligned on the buccal rim 110 and lingual rim 120 of the device. As shown in FIG. 2, outer flange 202 and inner flange 204 are constructed to keep oral tissues extended to improve light exposure. A controller (discussed in reference to FIG. 5) can control the amplitude and frequency of the light-rays in addition to oscillations between red, near-infrared and blue wavelength exposure. Oral appliance 100 exposes virtually all internal tissues of the mouth including the buccal, palatal, lingual and sub-lingual tissues to the light waves generated by the light source at virtually the same time.

Antenna 130 equipped with a universal serial bus (USB) connector 132 that allows for control of application of specific light rays and exposure to intra-mouth tissue via LEDs 104 in appliance 100. This permits wired or wireless control of appliance 100.

Oral appliance 100 in one embodiment has the shape of a mouth guard having a bite plane 140 for receipt of the upper and lower teeth of a patient for situating appliance 100 in the mouth in a secure and predictable manner. In one embodiment appliance 100 has an outer circumference of approximately 120 millimeters, but sizes can vary with a circumference in the 90 to 150 millimeter range for users of different sizes. In an embodiment bite plane 140 has a width a of approximately 12 millimeters, although size here can vary.

Oral appliance 100 in an embodiment comprises a clear silicone material that has embedded into it the LED lights 104 or a microprocessor chip that provides optimal light delivery. This embedded configuration completely seals the power harness 502 (FIG. 5) for maximum moisture control. In addition to delivery of red and near-infrared light waves, according to an embodiment of the present invention blue light waves are also delivered. blue light waver have been shown to have a strong anti-microbial effect producing a controlled antiseptic environment to the oral cavity that promotes healing. Also, unlike existing appliances, the presently described oral appliance delivers highly adjustable light wave intensities and a wider range of wavelengths all of which are necessary to optimize tissue healing and bone growth. A host of oral conditions are chronic and inflammatory in nature and are usually associated with autoimmune deficiencies (e.g., lichen planus). Such conditions have no cure so current treatments are only palliative. Recent research has shown that exposure to specific light in the infrared/red range has a healing and stabilizing effect on these tissues. Such treatments make patients with these conditions more comfortable and offer long-term relief.

In addition to the autoimmune diseases addressed by the present invention, the device treats Periodontal Disease—the most common disease in mankind. This condition has no cure, but the inter-oral device's enhanced light therapy has shown promising results in the management and treatment of Periodontal Disease. Clinicians testing the device believe this success is due in large part to the enhanced exposure of diseased tissue to the infrared/red light spectrum afforded by the device.

Researchers have concluded that the septic and uncontrolled health of the oral cavity has an important impact on the overall health of patients. For example, diabetic patients have difficulty controlling their blood chemistry's when they present chronic septic oral conditions. Cardiac patients have significant blood enzyme level alterations when uncontrolled oral septic conditions and periodontal disease are present. These septic conditions are not simply of dental origin but are an entire oral cavity/periodontium complex. Routine dental office hygiene visits cannot adequately treat these conditions, which require additional daily maintenance through the light therapy produced by the device.

Additional uses for this light photo therapy are the treatment of:

Chronic apthous ulcers

Generalized oral desquamative conditions

Chronic visculous/bulous diseases

Enhanced healing of laser guided tissue regenerated therapy

Adjunctive plaque/bacterial control in adolescent Orthodontic patients

Pain control in active Orthodontic therapy patients

Orthognathic surgical patients will have enhanced healing and bacterial control

Post-op Periodontal surgical patient healing and pain control.

Chronic generalized root sensitive pain control.

Healing and pain management of oral trauma patients.

Reduction of blood serum bacterial levels in patients that have metal joint replacements Reduction or elimination of the need for prophylactic antibiotic therapy before dental treatment on patients required by AHA guidelines.

Accelerated bone growth.

Figure 3:
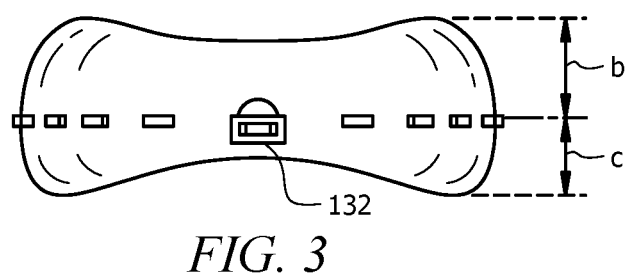
FIG. 3 depicts a rear view of an intra-oral appliance according to an embodiment of the present invention.
Figure 4:
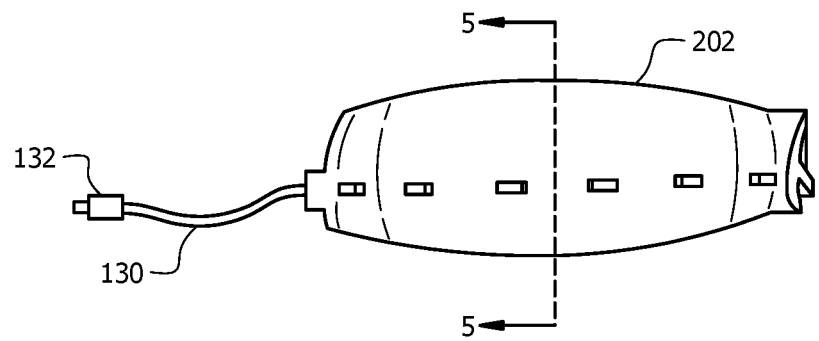
FIG. 4 depicts a side view of an intra-oral appliance according to an embodiment of the present invention.

FIG. 3 depicts a front view of oral appliance 100. As shown an upper portion of appliance 100 from USB port 132 to the upper edge of outer flange 202 in one embodiment is approximately 11 millimeters (see b), although sizes can vary. The lower portion of appliance 100 from USB port 132 to the farthest point of outer flange 202 is approximately 7 millimeters (see c) in one embodiment, although this distance can vary. Note that front profile of oral appliance 100 is oblong in a figure-8 like shape. FIG. 4 depicts a side view of oral appliance 100. Note that from the side oral appliance 100 is substantially of an oblong and oval shape.

Figure 5:
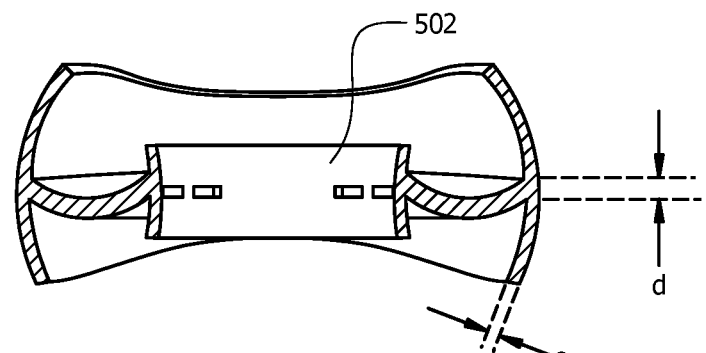
FIG. 5 depicts a cross sectional view of an intra-oral appliance according to an embodiment of the present invention.

FIG. 5 depicts a cross sectional view of oral appliance 100 with reference to points S-S in FIG. 4. The front portion of oral appliance 100 comprises power harness 502 that is embedded in silicone of outer flange 200. In one embodiment, the width of bite plane (see d) is approximately two millimeters but the width can be between 1.5 and 2.5 millimeters. Outer flange as shown in one embodiment has a thickness of approximately 0.8 millimeters (see e), although the thickness can vary between 0.6 millimeters and 1 millimeter.

Figure 6:
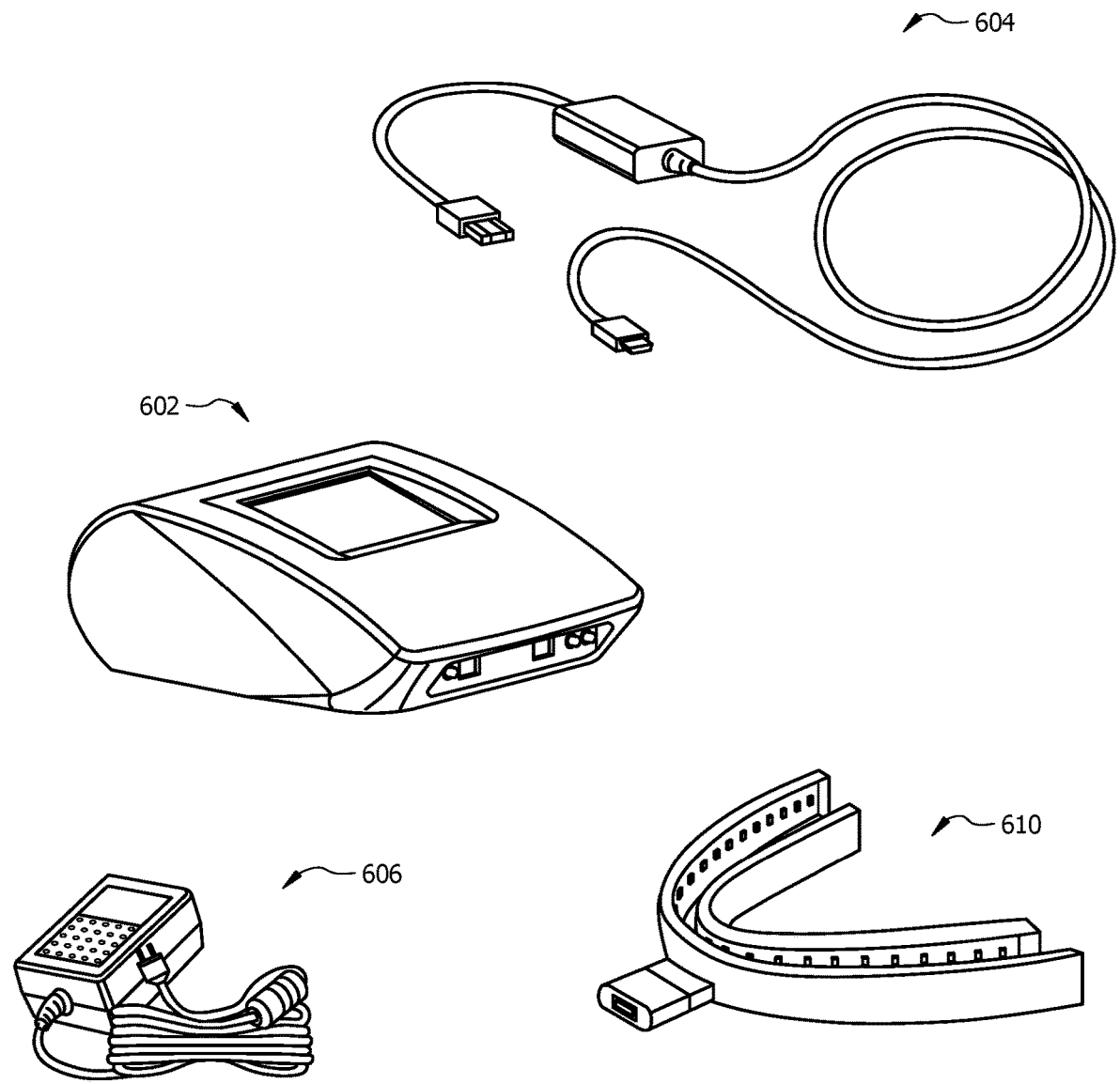
FIG. 6 depicts a perspective view of components of an intra-oral appliance system according to an embodiment of the present invention.

FIG. 6 depicts components of an intra-oral appliance system according to an embodiment of the present invention. As shown in FIG. 6, the intra-oral appliance system in one embodiment is comprised of PBT controller 602, converter box and interface cable 604, universal input A/C adapter 606 and mouthpiece 610. In one embodiment, mouthpiece 610 shares the features of oral appliance 200. In another embodiment, mouthpiece 610 comprises the features as described below. Mouthpiece 610 includes red and blue LEDs for near infrared reflectance (NIR) spectroscopy to analyze characteristics of the tooth and gums. These components enable operator control through controller 602 of the frequency and amplitude of light emitted from the LEDs housed in mouthpiece 610 when mouthpiece 610 is intra-oral.

Figure 7:
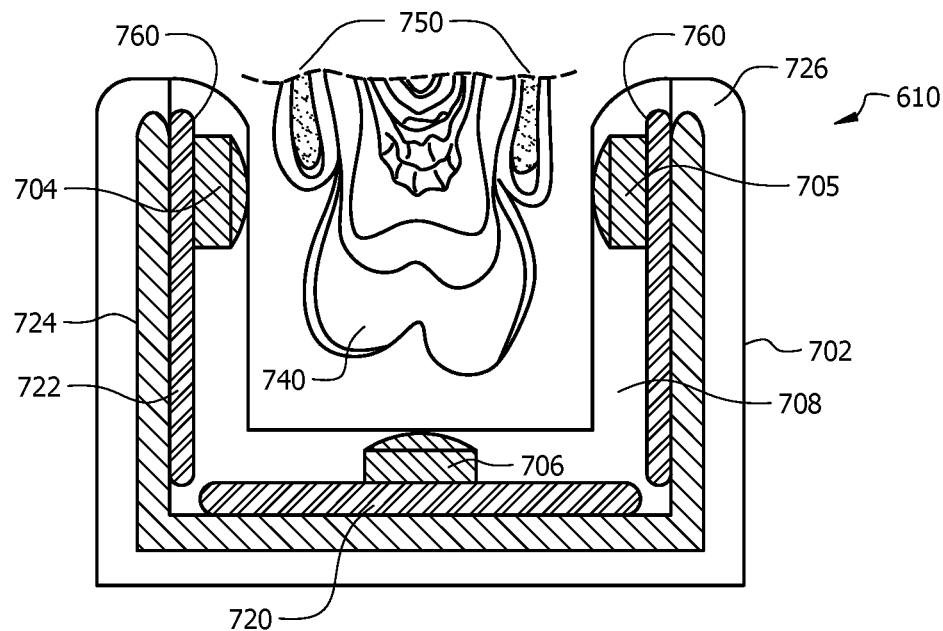
FIG. 7 depicts a cross sectional view of a mouthpiece of an intra-oral appliance system according to an embodiment of the present invention.

FIG. 7 depicts a cross sectional view of mouthpiece 610 of an intra-oral appliance system according to an embodiment of the present invention. As shown in FIG. 7, mouthpiece 610 comprises an outer side 702 and inner side 703. Inner side 703 of a mouthpiece 610 surrounds tooth 740 and gums 750. Outer side 702 and inner side 702 of mouthpiece 610 are correspond to outer flange 202 and inner flange 204 of FIG. 2 but more detail is provided in this FIG. 7. The inner side 703 of mouthpiece 610 comprises a pair of gum LEDs 704 and 705 and molar LED 706 within pre-molded silicone in the form of inner silicone cover 708. Gum LED 705 and molar LED 706 are associated with first flexible printed circuit board (PCB) 720. Gum LED 704 is associated with second flexible PCB 722. First flexible PCB 720 and second flexible PCB 722 are associated with carrier 724. This arrangement permits collection of near-infrared (NIR) data by mouthpiece 610 and delivery of data to PBT controller 602 for further analysis. The exterior of the mouthpiece 610 is covered or housed by a transparent outer silicone case 726. First PCB 720 and second PCB 722 of mouthpiece 610 are coated with silicone pre-mold 760. Outer silicone case 726 and inner silicone cover 708 can be pre-molded silicone or made of injection molded silicone.

In one embodiment of the mouthpiece of the present invention, an outer (gum and molar) mouthpiece component can include 36 red LEDs and 36 NIR LEDs and an inner (gum) mouthpiece component can include 24 blue LEDs and 36 NIR LEDs. "Outer" in this regard refers to the outside face of the gums and molars while "inner" refers to the side of the gums and molars facing the inside of the mouth. Red/NIR LED wavelength is in the 645-850 nm range. Blue/NIR LED wavelength is in the 460-850 nm range.

Figure 8:
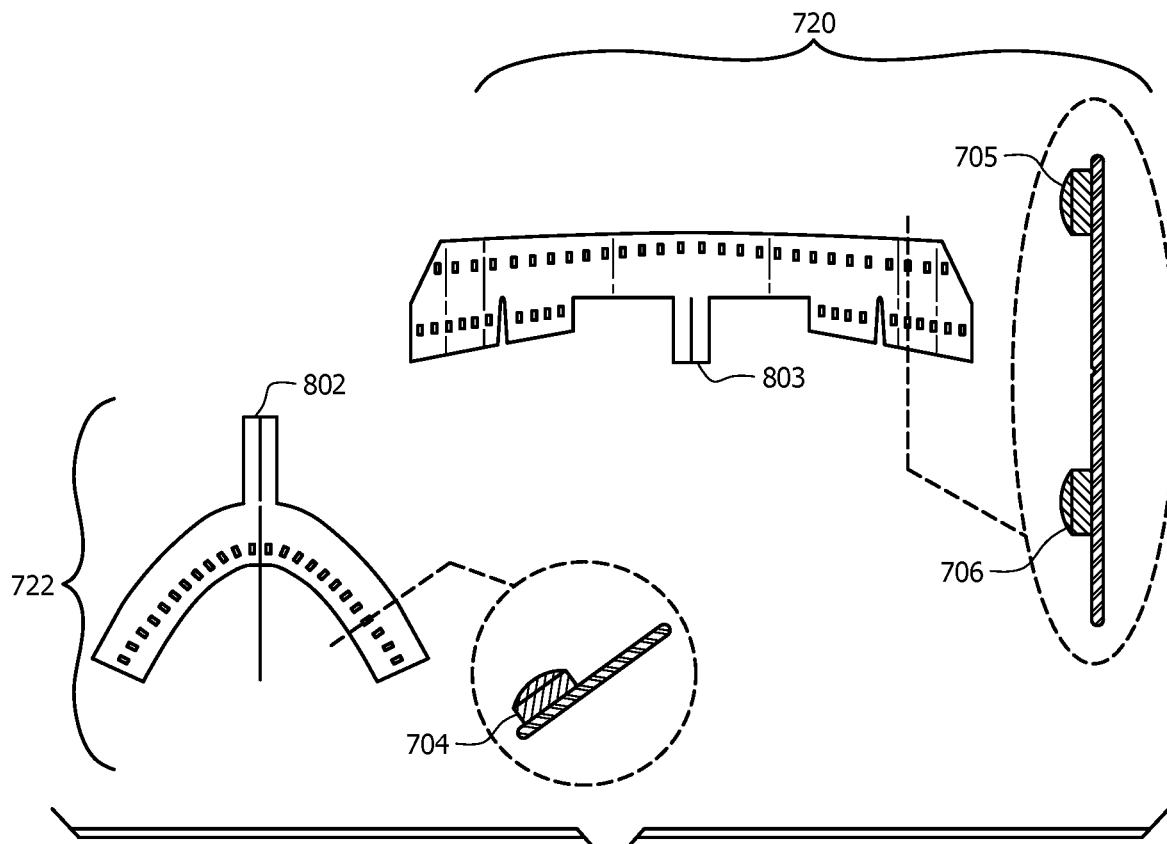
FIG. 8 depicts an aspect of a method for mouthpiece assembly of an intra-oral appliance system according to an embodiment of the present invention.

FIG. 8 depicts an aspect of a method for mouthpiece assembly of an intra-oral appliance system according to an embodiment of the present invention. FIG. 8 depicts the various flexible PCBs that comprise the components of mouthpiece 610 when in use and associated with the inner jaw and outer jaw. As shown, each component of mouthpiece 610 comprises portions of PCBs containing a plurality of red and blue LEDs placed on flexible PCB portions using surface-mount technology (SMT). The inside and outer components of the mouthpiece in flat form are shown in FIG. 8 with first PCB 720 portion associated with the outer jaw comprising a PCB tongue 803. First PCB 720 has associated gum LED 705 and molar LED 706. Second PCB 722 associated with the inside jaw also includes a corresponding PCB tongue 802. Second PCB 722 portion has associated gum LED 704. When first PCB 720 and second PCB 722 are joined as shown in FIG. 7, tongues 802 and 803 will be joined. As discussed with the respect to FIG. 7, second PCB 722 has mounted on it one gum LED 704 and first PCB 720 portion of the mouthpiece for the outer jaw has upon it mounted a second gum LED 705 and a molar LED 706, as shown in the respective cross-sectional views in FIG. 8.

Figure 9:
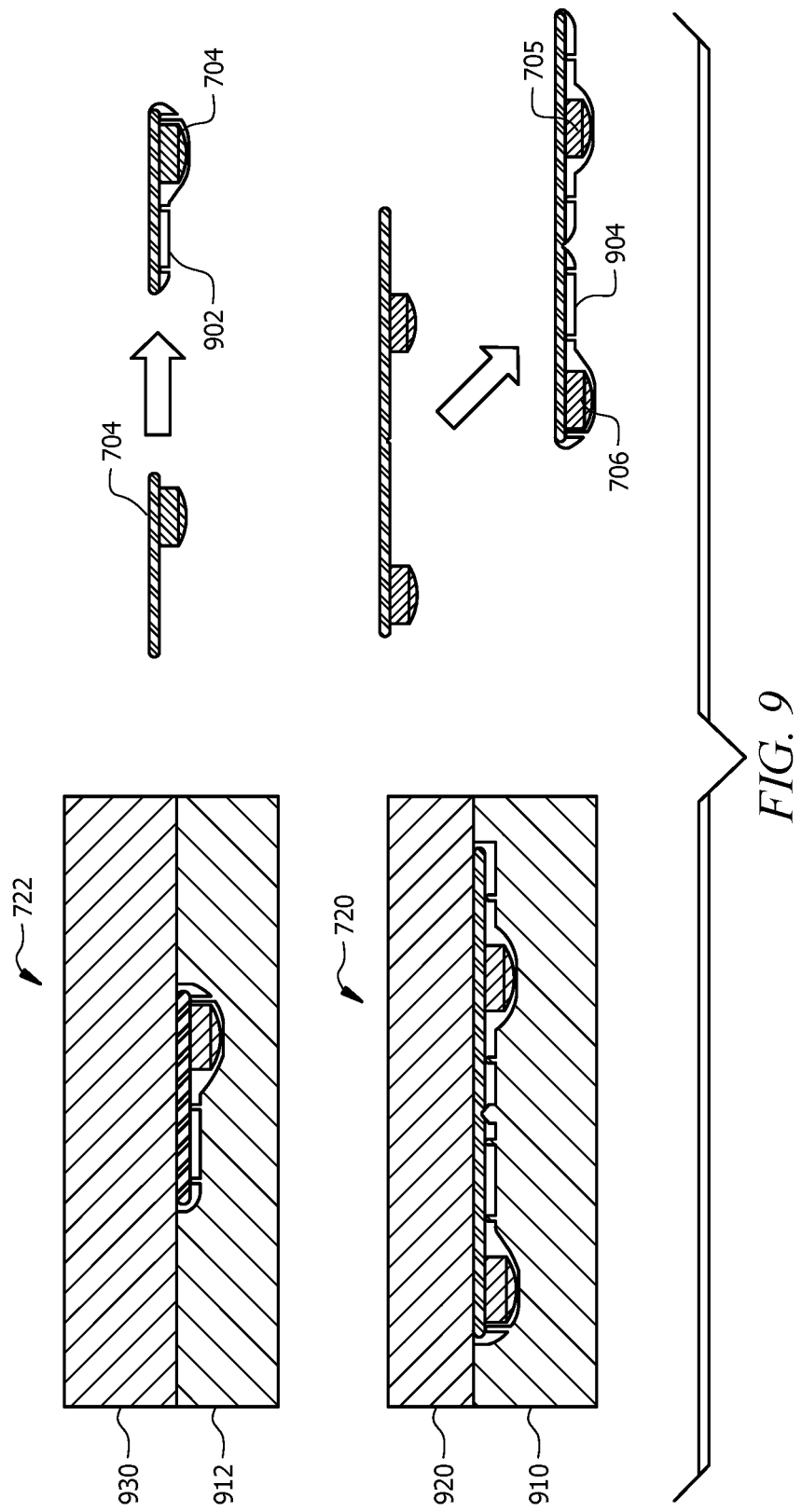
FIG. 9 depicts an aspect of a method for mouthpiece assembly of an intra-oral appliance system according to an embodiment of the present invention.

FIG. 9 depicts an aspect of a method for mouthpiece assembly of an intra-oral appliance system according to an embodiment of the present invention. In this step, pre-molded SMT flexible PCB has disposed thereon a transparent silicone layer. As shown in FIG. 9, second PCB 722 associated with the inside jaw has disposed thereon the one gum LED 704 with transparent silicone pre-mold 902 covering that LED 704. Similarly, first PCB 720 associated with the outer jaw has disposed thereon gum LED 705 and molar LED 706 with transparent silicone pre-mold 904 covering LEDs 705 and 706. These arrangements having the transparent silicone pre-molds 902 and 904 are the respective PCB bottom pre-molds, with PCB bottom pre-mold 910 for first PCB 720 and PCB bottom pre-mold 912 for second PCB 722. Associated with each bottom pre-mold is a PCB top pre-mold, with PCB top pre-mold 920 for first PCB 720 and PCB top pre-mold 930 for second PCB 722, each disposed above the respective bottom pre-mold for each.

Figure 10:
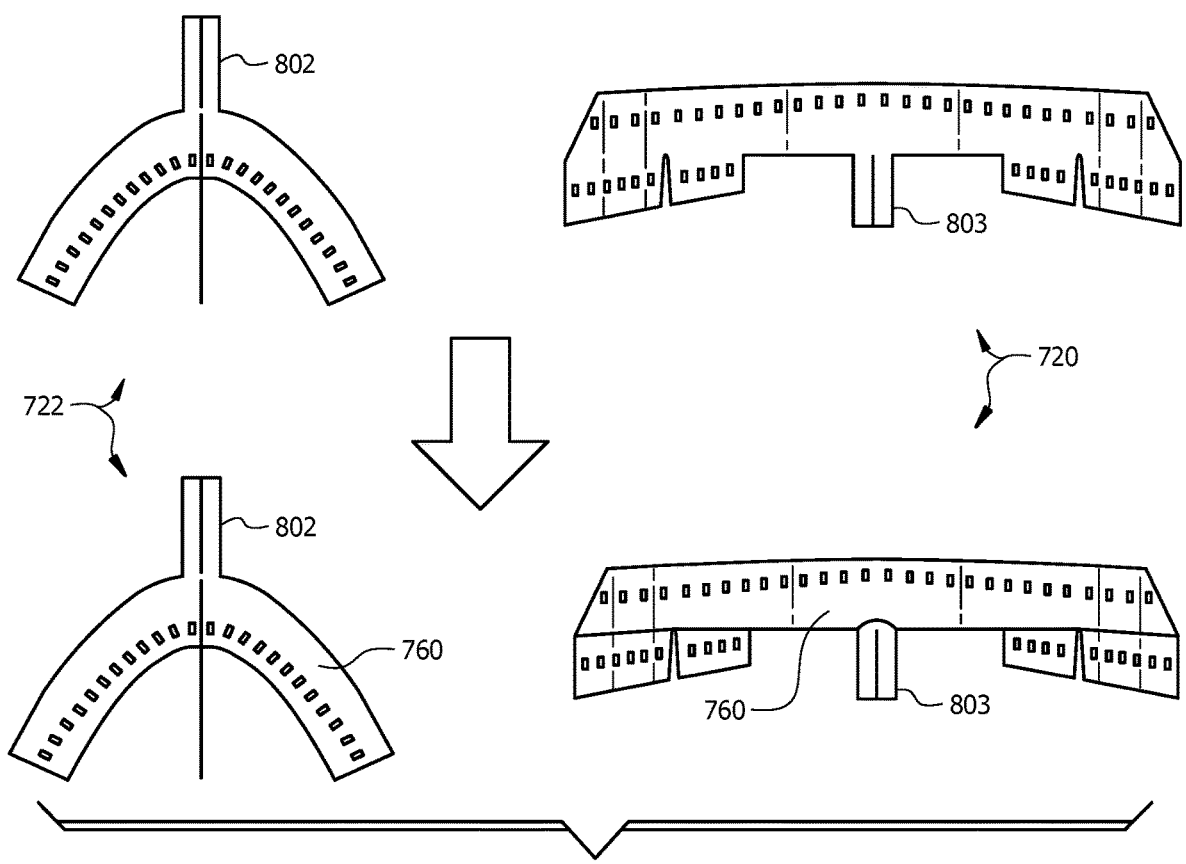
FIG. 10 depicts an aspect of a method for mouthpiece assembly of an intra-oral appliance system according to an embodiment of the present invention.

FIG. 10 depicts another aspect of a method for mouthpiece assembly of an intra-oral appliance system according to an embodiment of the present invention. In FIG. 10, the resulting mouthpiece 610 components first PCB 720 and second PCB 722 are shown before and after the pre-mold application steps described with respect to FIG. 9 are completed. As shown first PCB tongue 803 and second PCB tongue 802 remain uncoated while the remaining portions of first PCB 720 and second PCB 722 of mouthpiece 610 are coated with the silicone pre-mold 760.

Figure 11:
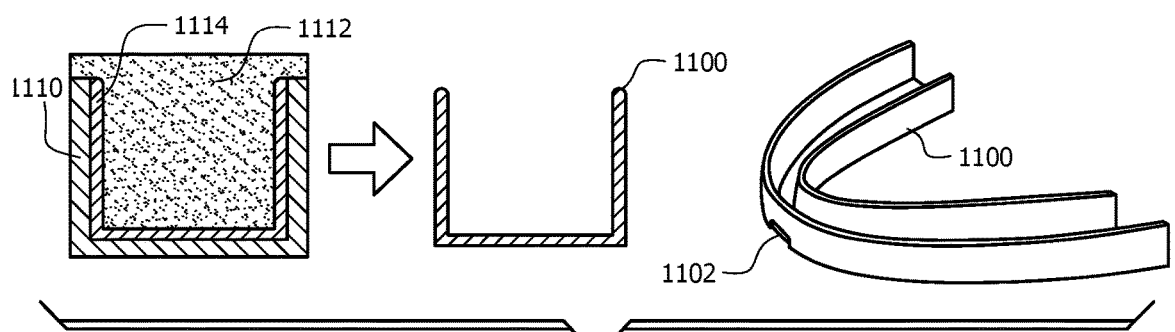
FIG. 11 depicts an aspect of a method for mouthpiece assembly of an intra-oral appliance system according to an embodiment of the present invention.

FIG. 11 depicts another aspect of a method for mouthpiece assembly of an intra-oral appliance system according to an embodiment of the present invention. In FIG. 11, the fabrication process of the outer silicone case for mouthpiece 610 is shown. The fabrication process includes a top mold chase 1110 and a bottom mold chase 1112 used in an injection mold operation. Between each chase is an injection cavity 1114 in which silicone is injected. The resulting outer silicone case 1100 is shown, having opening 1102 though which tongues 802 and 803 will be inserted later during construction of completed mouthpiece 610.

Figure 12:
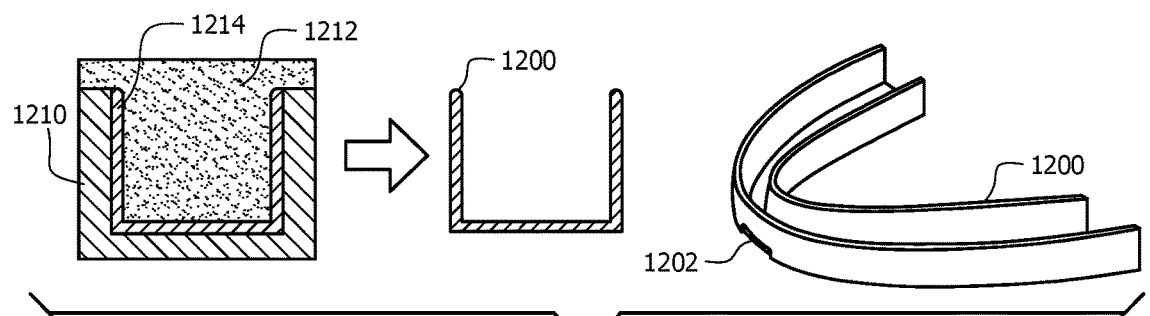
FIG. 12 depicts an aspect of a method for mouthpiece assembly of an intra-oral appliance system according to an embodiment of the present invention.

FIG. 12 depicts an aspect of a method for mouthpiece 610 assembly of an intra-oral appliance system according to an embodiment of the present invention. In FIG. 12, construction of a pre-mold silicone carrier is described. Again, top and bottom chases 1210 and 1212 are used to create injection cavity 1214 for injection of silicone to create the resulting carrier 1200. Like the outer silicone case 1100, carrier 1200 includes opening 1202 that corresponds to opening 1102 in the outer silicone case for receiving tongues 802 and 803.

Figure 13:
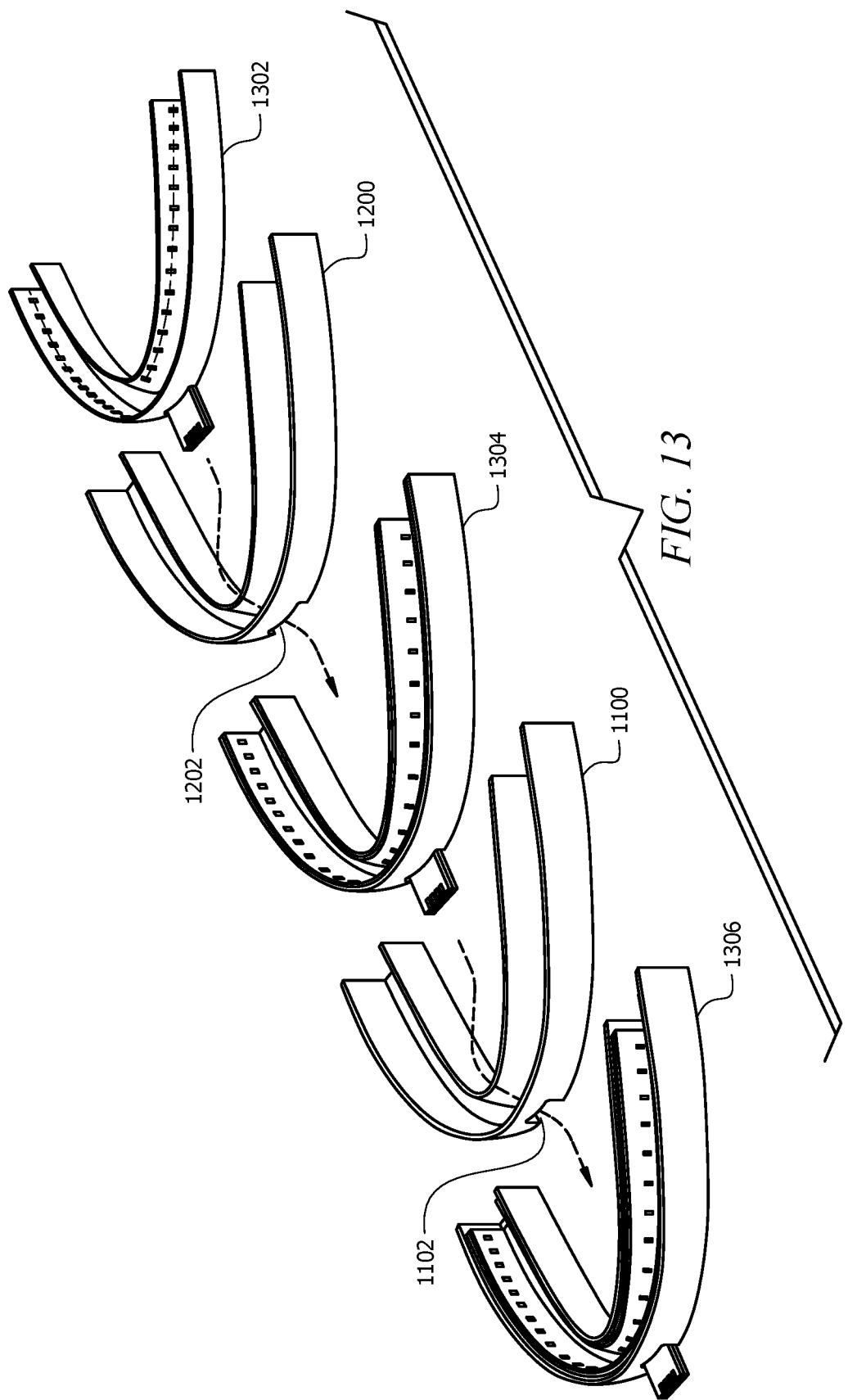
FIG. 13 depicts an aspect of a method for mouthpiece assembly of an intra-oral appliance system according to an embodiment of the present invention.

FIG. 13 depicts an aspect of a method for mouthpiece assembly of an intra-oral appliance system according to an embodiment of the present invention. In this step of the process, assembly of the various layers of mouthpiece 610 is shown. Dual PCB module 1302 (the structure of which is described in FIG. 8) is inserted into carrier 1200 resulting in PCB-carrier module 1304. PCB carrier module 1304 in turn is inserted into outer silicone case 1100 to form resulting pre-encapsulated module 1306. Note that tongues 802 and 803 are inserted into corresponding opening 1202 in carrier 1200 and opening 1102 in outer silicone case 1100. This process will be described in more detail below in connection with the various steps of FIGS. 14-18.

Figure 14:
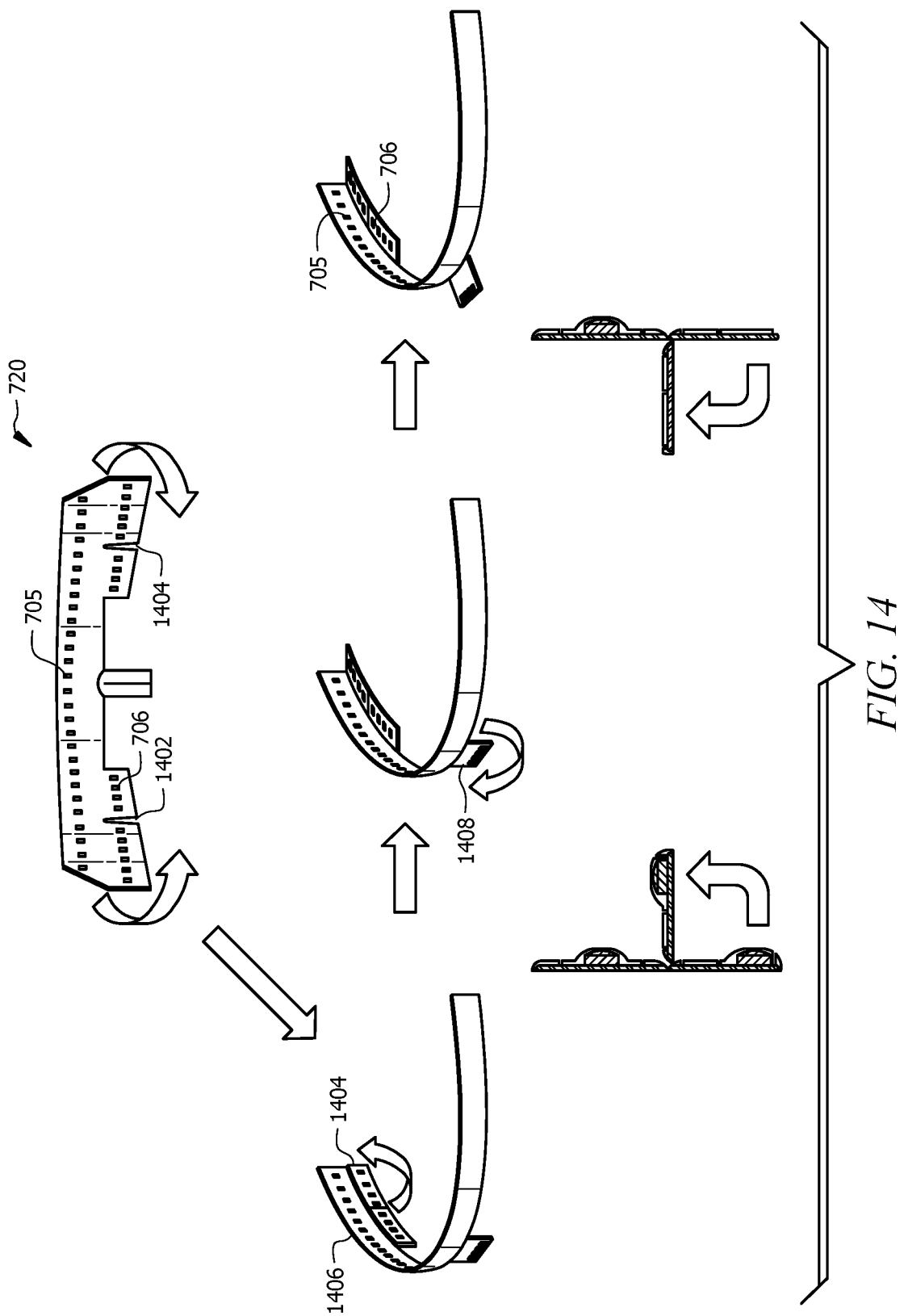
FIG. 14 depicts a bending process for mouthpiece assembly of an intra-oral appliance system according to an embodiment of the present invention.

FIG. 14 depicts a bending process for mouthpiece 610 assembly of an intra-oral appliance system according to an embodiment of the present invention. As shown in FIG. 14, flat first PCB 720 that corresponds to the front of the jaw includes gum LEDs 704 and molar LEDs 705, as described. Flat first PCB 720 is bent into a horseshoe configuration. Then, wings 1402 and 1404 of first PCB 720 are bent inward at approximately a right angle in relation to the gum LED PCB flex portion 1406. Next, tongue 1408 (comprised of tongues 802 and 803) is bent outward. Cross-section views in FIG. 14 showing the wing inward bends (before and after) and tongue outward bend (before and after) are provided.

Figure 15:
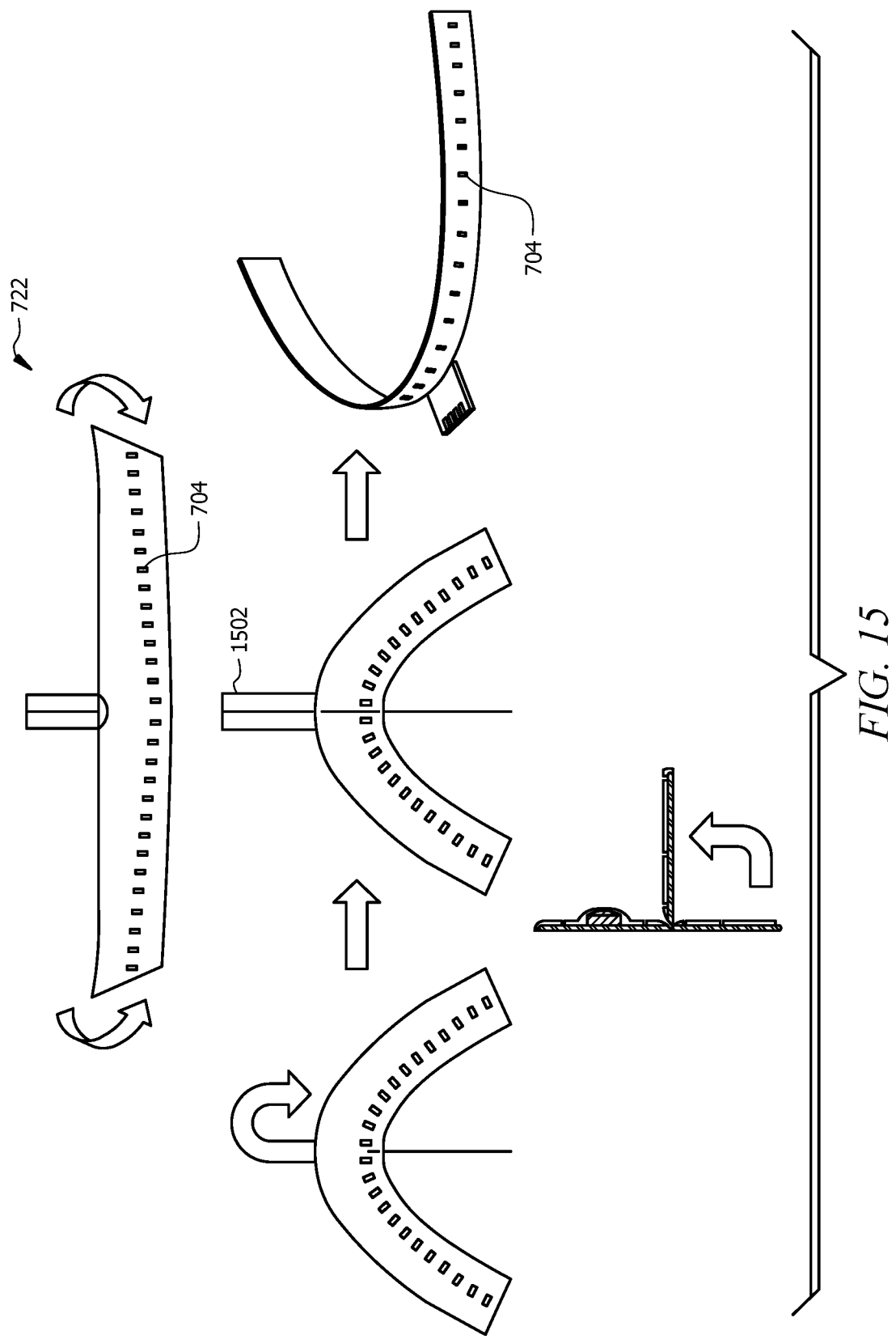
FIG. 15 depicts a bending process for mouthpiece assembly of an intra-oral appliance system according to an embodiment of the present invention.

FIG. 15 depicts a bending process for mouthpiece assembly of an intra-oral appliance system according to an embodiment of the present invention. In this step, flat second PCB 722 corresponding to the inside jaw portion of mouthpiece 610 is bent, first into a horseshoe. Long tongue 1502 is bent inward. The cross-sectional view of the resulting second PCB 722 section of mouthpiece 610 before and after the inward bend of long tongue 1502 is shown.

Figure 16:
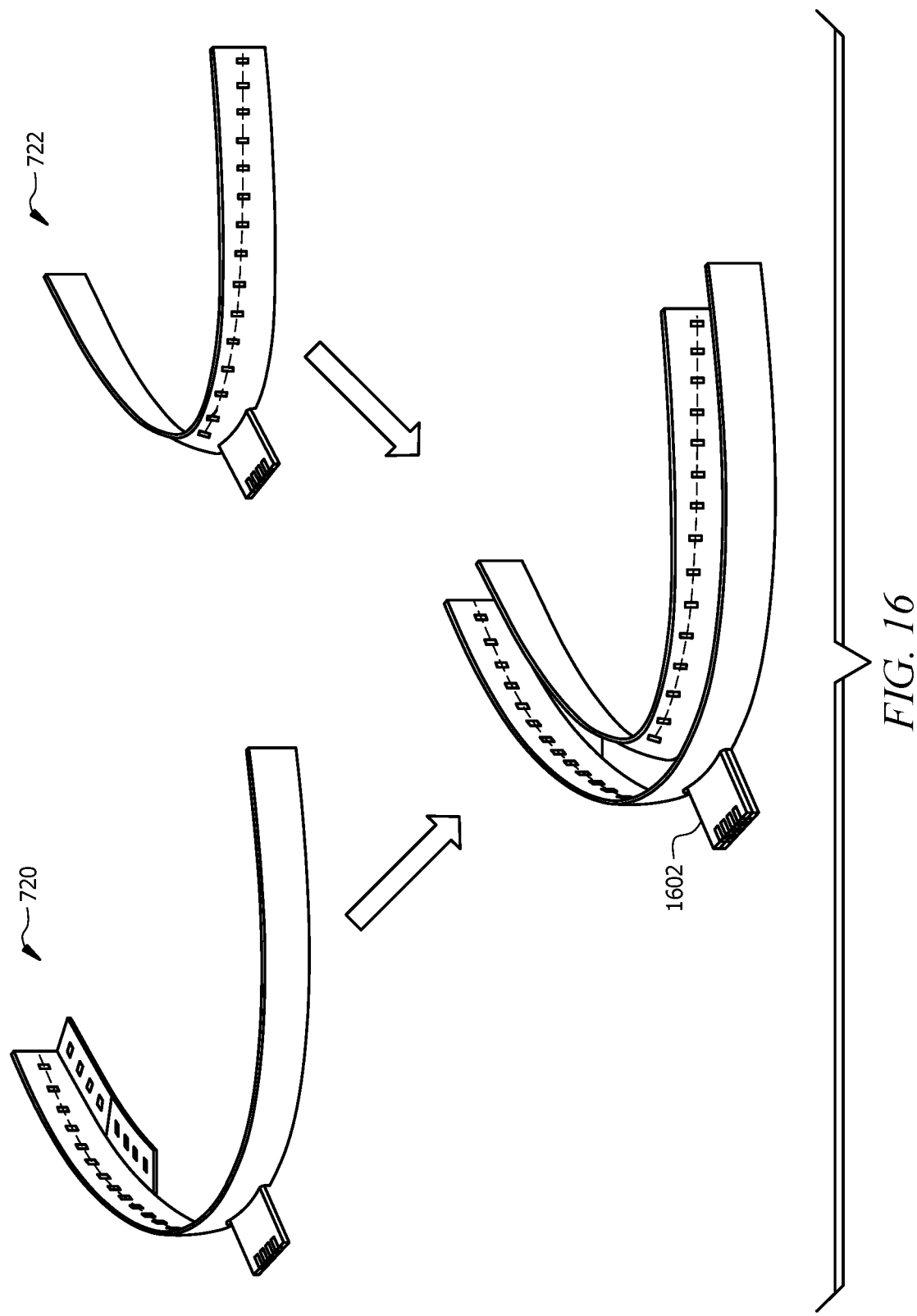
FIG. 16 depicts a module assembly process of an intra-oral appliance system according to an embodiment of the present invention.

FIG. 16 depicts a module assembly process of an intra-oral appliance system according to an embodiment of the present invention. In this step, dual-PCB module assembly is completed by combining bent first PCB 720 and second PCB 722 modules as described in previous steps. Each of bent first PCB 720 and second PCB 722 are aligned with one another as shown with a dual layer tongue 1602 resulting from tongue 1408 from bent first PCB 720 (FIG. 14) and long tongue 1502 from bent second PCB 722 (FIG. 15). The resulting dual-PCB module incudes outer gum LEDs 705 and molar LEDs 706 associated with outer jaw first PCB 720, and inside gum LEDs 704 associated with inside jaw second PCB 722.

Figure 17:
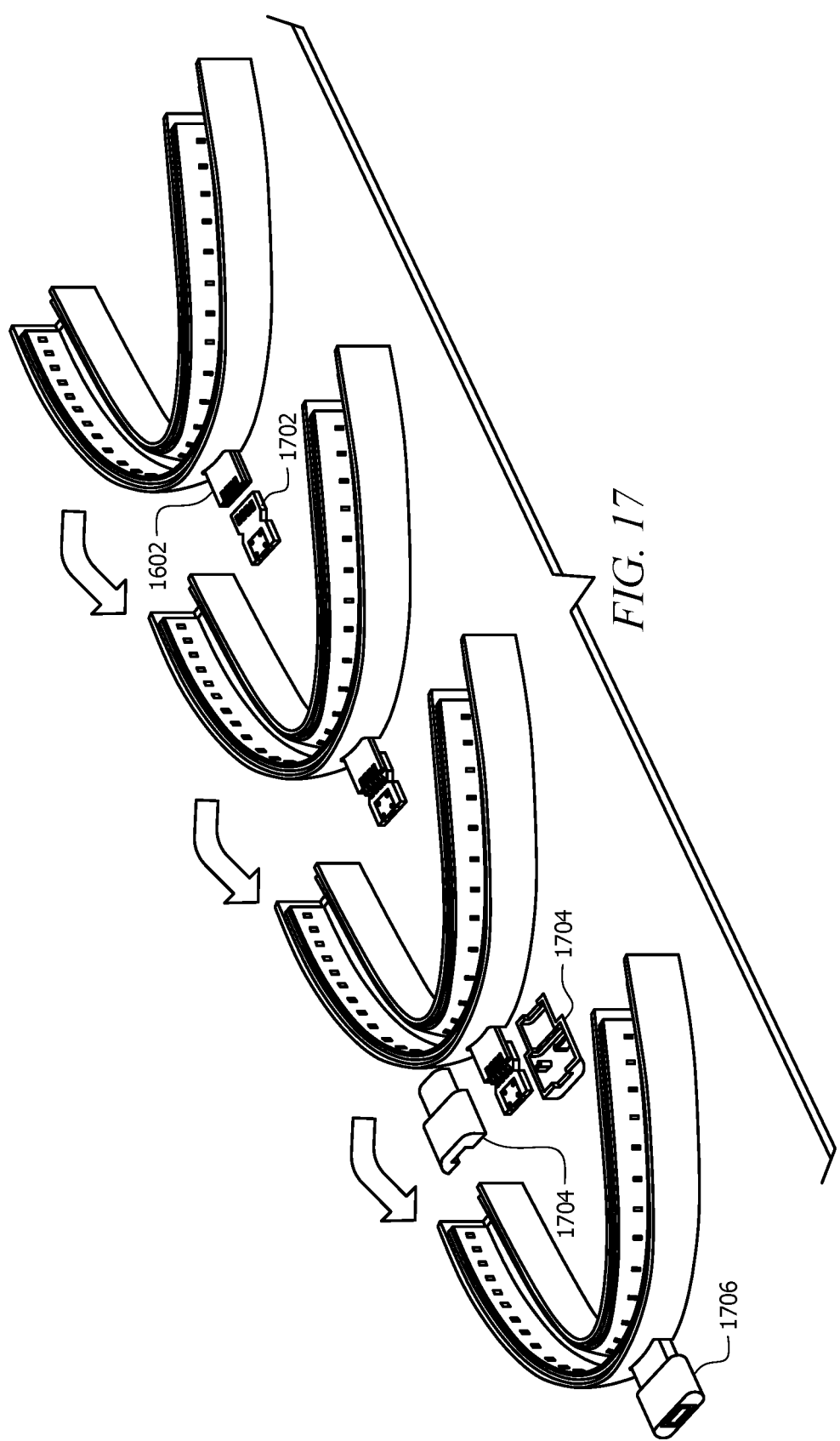
FIG. 17 depicts a PCB electrical interconnection process of an intra-oral appliance system according to an embodiment of the present invention.

FIG. 17 depicts a PCB electrical interconnection process of an intra-oral appliance system according to an embodiment of the present invention. In this step, electrical interconnection of the PCB is enabled. As shown, dual layer tongue 1602 is inserted into socket PCB and soldered. Then a single or two piece (as shown) USB enclosure 1704 is applied over dual layer tongue 1602 and socket 1702. A dual PCB module assembly having a micro USB connector 1706 associated with dual layer tongue 1602 results.

Figure 18:
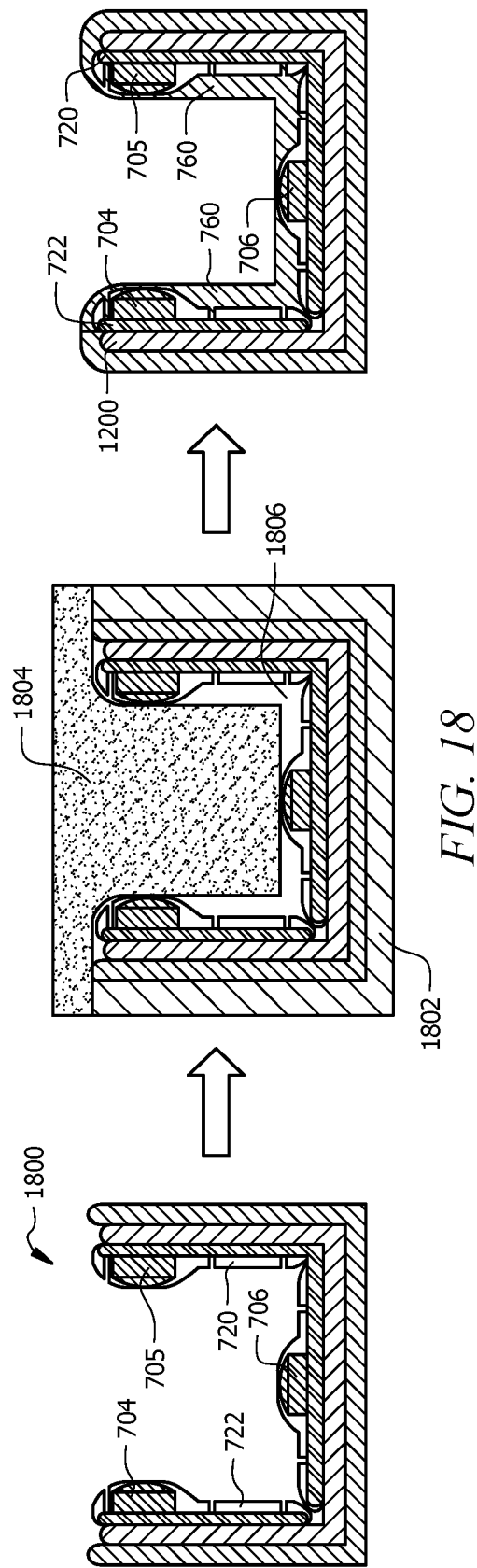
FIG. 18 depicts an aspect of a method for mouthpiece assembly of an intra-oral appliance system according to an embodiment of the present invention.

FIG. 18 depicts an aspect of a method for mouthpiece assembly of an intra-oral appliance system according to an embodiment of the present invention. In this step, the assembled dual PCB module assembly is encapsulated in silicone. As shown in FIG. 18, exposed LEDs, PCB and silicone carrier within outer silicone case are disposed within a top mold chase and bottom mold chase. The top and bottom mold chases leave an injection cavity on the interior side of dual PCB module, enabling silicone encapsulation of the exposed PCBs 720 and 722, exposed LEDs 704, 705 and 706 and silicone carrier 1200. After injection, the LEDs 704, 705 and 706, first PCB 720 and second PCB 722 and silicone carrier 1200 are fully encapsulated with injected silicone 760.

FIG. 19 provides perspective and cross-section views of the mouthpiece assembly resulting from the various steps herein described, both before and after silicone encapsulation. Assembled dual PCB 1800 after undergoing the described silicone injection process results in encapsulated mouthpiece 610, with LEDs 704, 705 and 706 and first PCB 720 and second PCB 722 coated with silicone. Mouthpiece 610 is now ready for use and its electrical components are not susceptible to damage from fluids from the user's mouth or otherwise.

In some of the embodiments shown, the various LEDs are disposed on the exterior of the mouthpiece on both the buccal and lingual sides of the mouthpiece. In other embodiments, the various LEDs are disposed on the interior of the mouthpiece both on the buccal and lingual sides and on the interior bite plane. In other embodiments, however, LEDs are disposed both on the interior and exterior sides of the mouthpiece on the buccal, lingual and/or bite plane.

Furthermore, the mouthpiece 610 disclosed and described in one embodiment is a single u-shaped piece that can be placed on either the top or bottom teeth and gums of the user. In another embodiment, a double-sided mouthpiece is described in which upper and lower buccal and lingual rims and flanges have disposed thereon LEDs on either the interior, exterior or both sides of the mouthpiece. In other words, the double-sided mouthpiece includes a combined upper mouthpiece and lower mouthpiece with LEDs disposed on the interior, exterior or both that allows the user at one time to receive light treatments to both the upper gums and molars and the lower gums and molars. The construction of the double-sided mouthpiece can be performed in two stages as described herein for the single sided mouthpiece, one for the upper and one for the lower half. In the alternative, the PCBs can serve as the backbone for a single body construction of the double-sided mouthpiece.

While the disclosed embodiments have been described with reference to one or more particular implementations, these implementations are not intended to limit or restrict the scope or applicability of the invention. Those having ordinary skill in the art will recognize that many modifications and alterations to the disclosed embodiments are available. Therefore, each of the foregoing embodiments and obvious variants thereof is contemplated as falling within the spirit and scope of the disclosed inventions.

While the invention has been particularly shown and described with reference to a preferred embodiment, it will be understood by those skilled in the art that various changes in form and detail can be made therein without departing from the spirit and scope of the invention.

Additional Description

The following clauses are offered as further description of the disclosed invention.

Clause 1. An intra-oral appliance for use inside of a mouth, comprising:
  a first printed circuit board comprising at least one light emitting diode positioned in a substantially opaque substrate for administering light waves on a first gum area and at least one light emitting diode for administering light waves on a tooth;
  a second printed circuit board comprising at least one light emitting diode positioned in a substantially opaque substrate for administering light waves on a second gum area;
  a first tongue extending from the center of the first printed circuit board and a second tongue extending from the center of the second printed circuit board;
  a substantially u-shaped printed circuit board carrier module having a slot in the center for receipt of the first tongue and the second tongue and the first printed circuit board and the second printed circuit board;
  a communication port connected to the first tongue and the second tongue for connection to a controller to provide control signals to the first printed circuit board and the second printed circuit board; and
  an outer transparent case encapsulating the substantially u-shaped printed circuit board carrier module containing the first printed circuit board and second printed circuit board,
  wherein the first printed circuit board and the second printed circuit board form a substantial u-shaped substrate.

Clause 2. The intra-oral appliance of any proceeding or preceding claim, wherein the substantially u-shaped printed circuit board carrier module comprises a buccal rim, a lingual rim and a bite plane.

Clause 3. The intra-oral appliance of any proceeding or preceding claim, wherein the at least one light emitting diode of the first printed circuit board and the at least one light emitting diode of the second printed circuit board emit red light.

Clause 4. The intra-oral appliance of any proceeding or preceding claim, wherein the at least one light emitting diode of the first printed circuit board and the at least one light emitting diode of the second printed circuit board emit near-infrared light.

Clause 5. The intra-oral appliance of any proceeding or preceding claim, wherein the at least one light emitting diode of the first printed circuit board and the at least one light emitting diode of the second printed circuit board emit blue light.

Clause 6. The intra-oral appliance of any proceeding or preceding claim, wherein the buccal rim and bite plane encompass the first printed circuit board.

Clause 7. The intra-oral appliance of any proceeding or preceding claim, wherein the lingual rim encompasses the second printed circuit board.

Clause 8. The intra-oral appliance of any proceeding or preceding claim, wherein the buccal rim has a thickness of approximately 0.8 millimeters.

Clause 9. The intra-oral appliance of any proceeding or preceding claim, wherein the buccal rim and the lingual rim are spaced at a distance of approximately 12 millimeters.

Clause 10. The intra-oral appliance of any proceeding or preceding claim, wherein the first gum area is a buccal side gum area.

Clause 11. The intra-oral appliance of any proceeding or preceding claim, wherein the second gum area is a lingual side gum area.

Clause 12. The intra-oral appliance of any proceeding or preceding claim, wherein the buccal rim has a height of approximately 18 millimeters.

Clause 13. The intra-oral appliance of any proceeding or preceding claim, further comprising an outer transparent casing encapsulating the first printed circuit board, the second printed circuit board and the the substantially u-shaped printed circuit board carrier module.

Clause 14. The intra-oral appliance of any proceeding or preceding claim, wherein the outer transparent casing comprises silicone.

Clause 15. A method of assembling an intra-oral appliance, comprising:
  connecting a first array of light emitting diodes to a first printed circuit board;
  connecting a second array of light emitting diodes to a second printed circuit board having a first end and a second end;
  bending the first printed circuit board into a substantial u-shape with the first array of light emitting diodes facing the interior of the substantial u-shape;
  folding a lower portion of the first printed circuit board upward to create a substantially right angle with an upper portion of the first printed circuit board;
  bending outward a first printed circuit board tongue;
  turning inward the first end and the second end of the second printed circuit board to form a substantial u-shape;
  bending outward a second printed circuit board tongue;
  forming a substantially u-shaped printed circuit board carrier module having a tongue slot by injecting silicone between an upper chase and a lower chase;
  inserting the bent first printed circuit board and the turned second printed circuit board into the substantially u-shaped printed circuit board carrier by inserted the first printed circuit board tongue and the second printed circuit board tongue into the printed circuit board carrier slot; and
  encapsulating the first printed circuit board and the second printed circuit board with a transparent silicone layer.

Clause 16. The method of any proceeding or preceding claim, wherein the step of encapsulating the first printed circuit board and the second printed circuit board comprises an injection molding process.

Clause 17. An intra-oral appliance system, comprising:
  a first printed circuit board comprising at least one light emitting diode positioned in a substantially opaque substrate for administering light waves on a first gum area and at least one light emitting diode for administering light waves on a tooth;
  a second printed circuit board comprising at least one light emitting diode positioned in a substantially opaque substrate for administering light waves on a second gum area;
  a first tongue extending from the center of the first printed circuit board and a second tongue extending from the center of the second printed circuit board;
  a substantially u-shaped printed circuit board carrier module having a slot in the center for receipt of the first tongue and the second tongue and the first printed circuit board and the second printed circuit board;
  a communication port connected to the first tongue and the second tongue for connection to a controller to provide control signals to the first printed circuit board and the second printed circuit board;
  an outer transparent case encapsulating the substantially u-shaped printed circuit board carrier module containing the first printed circuit board and second printed circuit board; and
  a controller in communication with the first printed circuit board and the second printed circuit board via the communication port, wherein the first printed circuit board and the second printed circuit board form a substantial u-shaped substrate.

What is claimed:

1. An intra-oral appliance for use inside of a mouth, comprising:
  a first printed circuit board comprising a first light emitting diode positioned in a substantially opaque substrate for administering light waves on a first gum area and a second light emitting diode for administering light waves on a tooth;
  a second printed circuit board comprising a third light emitting diode positioned in the substantially opaque substrate for administering light waves on a second gum area;
  a first tongue extending from the center of the first printed circuit board and a second tongue extending from the center of the second printed circuit board;
  a substantially u-shaped printed circuit board carrier module comprising a buccal rim, a lingual rim and a bite plane and having a slot in the center for receipt of the first tongue and the second tongue and the first printed circuit board and the second printed circuit board;
  a communication port connected to the first tongue and the second tongue for connection to a controller to provide control signals to the first printed circuit board and the second printed circuit board; and
  the substantially opaque substrate and an outer transparent case encapsulating the substantially u-shaped printed circuit board carrier module containing the first printed circuit board and the second printed circuit board, wherein the first printed circuit board and the second printed circuit board form a substantially u-shaped substrate, a fourth light emitting diode positioned in the outer transparent case;
wherein the fourth light emitting diode is disposed exterior of the buccal rim for administering light waves to an exterior gum and a cheek area inside of a mouth.

2. The intra-oral appliance of claim 1, wherein the first light emitting diode of the first printed circuit board and the third light emitting diode of the second printed circuit board emit red light.

3. The intra-oral appliance of claim 1, wherein the first light emitting diode of the first printed circuit board and the third light emitting diode of the second printed circuit board emit near-infrared light.

4. The intra-oral appliance of claim 1, wherein the first light emitting diode of the first printed circuit board and the third light emitting diode of the second printed circuit board emit blue light.

5. The intra-oral appliance of claim 1, wherein the buccal rim and bite plane encompass the first printed circuit board.

6. The intra-oral appliance of claim 1, wherein the lingual rim encompasses the second printed circuit board.

7. The intra-oral appliance of claim 1, wherein the buccal rim has a thickness in the range of 0.6 to 1.0 millimeters.

8. The intra-oral appliance of claim 1, wherein the buccal rim and the lingual rim are spaced at a distance of 12 millimeters.

9. The intra-oral appliance of claim 1, wherein the second gum area is a lingual side gum area.

10. The intra-oral appliance of claim 1, wherein the buccal rim has a height of 18 millimeters.

11. The intra-oral appliance of claim 1, wherein the outer transparent case comprises silicone.

12. An intra-oral appliance system, comprising:
a first printed circuit board comprising a first light emitting diode positioned in a substantially opaque substrate for administering light waves on a first gum area and a second light emitting diode for administering light waves on a tooth;
a second printed circuit board comprising a third light emitting diode positioned in an opaque substrate for administering light waves on a second gum area;
a first tongue extending from the center of the first printed circuit board and a second tongue extending from the center of the second printed circuit board;
a substantially u-shaped printed circuit board carrier module comprising a buccal rim, a lingual rim and a bite plane and having a slot in the center for receipt of the first tongue and the second tongue and the first printed circuit board and the second printed circuit board;
a communication port connected to the first tongue and the second tongue for connection to a controller to provide control signals to the first printed circuit board and the second printed circuit board;
the substantially opaque substrate and an outer transparent case encapsulating the substantially u-shaped printed circuit board carrier module containing the first printed circuit board and second printed circuit board; and a controller in communication with the first printed circuit board and the second printed circuit board via the communication port, wherein the first printed circuit board and the second printed circuit board form a substantially u-shaped substrate,
a fourth light emitting diode positioned in the outer transparent case;
wherein the fourth light emitting diode is disposed exterior side the buccal rim for administering light waves to an exterior gum and a cheek area inside of a mouth.

* * * * *